United States Patent [19]

Slinkard

[11] 4,201,868

[45] May 6, 1980

[54] REACTION OF METHANOL WITH SYNTHESIS GAS

[75] Inventor: William E. Slinkard, Corpus Christi, Tex.

[73] Assignee: Celanese Corporation, New York, N.Y.

[21] Appl. No.: 772,368

[22] Filed: Feb. 25, 1977

Related U.S. Application Data

[63] Continuation-in-part of Ser. No. 611,117, Sep. 8, 1975, abandoned, which is a continuation-in-part of Ser. No. 555,646, Mar. 5, 1975, abandoned.

[51] Int. Cl.$^2$ .................... C07C 67/36; C07C 69/14
[52] U.S. Cl. ............................ 560/232; 568/594; 568/487; 568/902
[58] Field of Search .......... 260/488 K, 601 R, 615 A; 560/232; 568/594

[56] References Cited

U.S. PATENT DOCUMENTS

| | | | |
|---|---|---|---|
| 2,457,204 | 12/1948 | Brooks ................................ | 560/232 |
| 2,727,902 | 12/1951 | Reppe et al. .................... | 260/488 K |
| 2,805,248 | 9/1957 | Friederich et al. .................. | 560/232 |
| 3,014,962 | 12/1961 | Reppe et al. .................... | 260/488 K |

FOREIGN PATENT DOCUMENTS

890949  9/1953  Fed. Rep. of Germany ........... 560/232

Primary Examiner—Vivian Garner
Attorney, Agent, or Firm—Stewart N. Rice; Ralph M. Pritchett

[57] ABSTRACT

A process for the reacting of methanol with carbon monoxide and hydrogen to produce increased amounts of methyl acetate, acetaldehyde and dimethyl acetal utilizing a catalyst comprising a cobalt carbonyl in complex with an organic nitrogen ligand.

6 Claims, No Drawings

REACTION OF METHANOL WITH SYNTHESIS GAS

BACKGROUND OF THE INVENTION

This is a continuation-in-part of co-pending U.S. Pat. application Ser. No. 611,117 filed Sept. 8, 1975, which in turn is a continuation-in-part of application Ser. No. 555,646 filed Mar. 5, 1975 and both now abandoned.

The liquid phase homogenous reaction of methanol with synthesis gas (a mixture of hydrogen and carbon monoxide) in the presence of a cobalt carbonyl catalyst to produce methyl acetate, acetaldehyde and dimethyl acetal is well known in the prior art; for example, see U.S. Pat. No. 2,457,204 issued Dec. 28, 1948 to Richard E. Brooks. The dimethyl acetal is formed by reaction between methanol and some of the acetaldehyde produced in the reaction, and is easily hydrolyzed to acetaldehyde and methanol. The use of a cobalt carbonyl catalyst has disadvantages in that in addition to the desired methyl acetate, acetaldehyde and dimethyl acetal (also known as 1,1-dimethoxy ethane), large quantities of other reaction products are produced such as ethanol, propanol, isopropanol, butanol, isobutanol, methane, carbon dioxide and methyl formate. Since the production of large amounts of by-products is economically undesirable, improvement in selectivity of the process toward the more valuable methyl acetate, acetaldehyde and/or dimethyl acetal is greatly to be desired. It is also known, as taught in U.S. Pat. No. 3,014,962, to employ as catalyst for this same purpose an iron-group metal, a ligand, and halide moiety. This, however, involves serious corrosion problems due to presence of the halide.

It is thus an object of the present invention to provide a new process for producing methyl acetate, acetaldehyde and dimethyl acetal. It is a further object to provide a new process for producing dimethyl acetal, acetaldehyde and methyl acetate from methanol and synthesis gas. A particular object is to improve the process wherein methanol and synthesis gas are reacted in the presence of a cobalt carbonyl catalyst whereby there results an increased selectivity toward the production of methyl acetate, acetaldehyde and dimethyl acetal and wherein the catalyst system is free of halide moiety. Additional objects will become apparent from the following description.

SUMMARY

The foregoing and other objects are accomplished by the present invention which in one aspect is an improvement in a process wherein methanol in the liquid phase is reacted at elevated temperatures and superatmospheric pressures with a gas comprised of carbon monoxide and hydrogen to produce a product comprising methyl acetate, acetaldehyde and dimethyl acetal, which improvement comprises utilizing a catalyst comprising a cobalt carbonyl in complex combination with an organic nitrogen ligand having at least one trivalent Lewis base nitrogen atom and which is free of halide moiety.

DETAILED DESCRIPTION OF THE INVENTION

As noted above, the present invention resides in the use of a nitrogen ligand modified cobalt carbonyl catalyst, that is the use of a catalyst comprising a cobalt carbonyl in complex combination with an organic nitrogen ligand. Such a nitrogen ligand modified cobalt carbonyl catalyst is known in the prior art for other reactions, for example, oxo reactions, and therefore the complex catalyst itself or method of preparing same does not constitute a part of the present invention. For a prior art use of a nitrogen ligand modified cobalt carbonyl catalyst see the article by Ryoji Iwanaga at *Bull. Chem. Soc. Japan,* 35, 865 (1962).

By the term "complex" as used in the specification and claims is meant a coordination compound formed by the union of one or more electronically rich molecules or atoms capable of independent existence with one or more electronically poor molecules or atoms, each of which is also capable of independent existence. By "ligand" is meant a compound having an element with a pair of electrons capable of forming a co-ordinate bond with a metal atom and which may simultaneously have the ability to accept electrons from the metal. The ligands useful in the present invention are organic nitrogen ligands, that is, those containing at least one trivalent nitrogen atom (sometimes herein called a Lewis base nitrogen atom) which possess a pair of electrons available for the formation of a coordinate bond with cobalt. The organic nitrogen ligand may contain, for example, from one to five Lewis base nitrogen atoms but preferably contains one to two, two Lewis base nitrogen atoms being especially preferred.

The organic nitrogen ligand may have other Lewis base atoms present although such is not preferred. Thus, a Lewis base oxygen atom such as from an hydroxyl, carboxyl, carbonyloxy, carbonyl or oxy group may be present in addition to the Lewis base nitrogen atom or atoms. Likewise, a Lewis base phosphorus arsenic, antimony, or sulfur atoms may be present. When Lewis base atoms other than nitrogen atoms are present, there are preferably no more than two of such other Lewis base atoms than the Lewis base nitrogen atoms. The ligand is preferably free of ethylenic and acetylenic unsaturation.

At least one of the three valences of the Lewis base nitrogen atoms present in the ligand must be satisfied with an organic group, with hydrogen satisfying any valences not satisfied by the organic groups. Preferably, the ligand is a urea compound or is a compound wherein all three valences of nitrogen are satisfied by a carbon to nitrogen linkage with an organic group (as in a tertiary amine, a nitrile or an heterocyclic aromatic nitrogen). Except for urea and substituted ureas, the ligands wherein one or two valences are satisfied with hydrogen (such as in a primary or secondary amine) do not give as good results as those organic nitrogen ligands having no hydrogen atoms attached to the Lewis base nitrogens.

A carbon atom satisfying one or more of the valences of the Lewis base nitrogen may be part of practically any organic group such as substituted and unsubstituted aliphatic, cycloaliphatic, aromatic or heterocyclic groups. Two different carbons of a single organic group may be bound to more than one of the valences of a nitrogen atom such that the nitrogen atom is a heterocyclic nitrogen in the ring of a heterocyclic compound as pyridine. Substitute groups may include carbonyl, carboxyl, nitro, amino, hydroxy, phospho, and the like.

The organic nitrogen ligand may contain in addition to carbon and the Lewis base nitrogen, various other atoms such as hydrogen, phosphorus, oxygen, arsenic, antimony and sulfur. Preferably, the organic nitrogen ligand (except for the urea compounds) will be composed of carbon, nitrogen and hydrogen. That is, they will contain at least one atom each of carbon, nitrogen and hydrogen and will contain no other type atoms. The urea compounds will, of course, additionally contain an oxygen atom. The Lewis base nitrogen atoms can be in various forms, such as amino nitrogens

nitrilo nitrogens ($\equiv$N) or heterocyclic nitrogens ($=$N—). Those organic nitrogen ligands having two nitrilo groups are especially preferred, such dinitriles preferably having from 3 to 18 carbon atoms.

The urea compounds useful in the invention are preferably those of the formula $R_2NCONR_2$ wherein R is hydrogen or a hydrocarbon group (preferably a $C_1$ to $C_9$ hydrocarbon group) free of ethylenic and acetylenic unsaturation and wherein each R may be alike or different. Thus, R could be hydrogen, alkyl, aryl, cycloalkyl, aralkyl, alkaryl and the like. It has been found that urea itself, $H_2NCONH_2$, is a very good ligand for practice of the invention.

The organic nitrogen ligands may contain a varying number of carbon atoms, for example, from 1 to 25 carbon atoms, although they generally will contain from about 1 to 18 carbon atoms.

Illustrative organic nitrogen ligands include by way of example: N,N,N',N'-tetramethylethylenediamine; N,N,N',N'-tetraethylethylenediamine; N,N,N',N'-tetra-n-propylethylenediamine; N,N,N',N'-tetramethylmethylenediamine; N,N,N',N'-tetraethylmethylenediamine; N,N,N',N'-tetraisobutylmethylenediamine; N-methylpiperazine; N-ethylpiperazine; 2-methyl-N-methylpiperazine, 2,2'-dipyridyl; methyl-substituted 2,2'-dipyridyl; ethyl-substituted 2,2'-dipyridyl; 1,4-diazabicyclo[2,2,2] octane; methyl-substituted 1,4-diazabicyclo[2,2,2]octane; 2-(dimethylamino)pyridine; 1,10-phenanthroline; methyl-substituted 1,10-phenanthroline; 2-(dimethylamino)-6-methoxyquinoline; 4-triethylsilyl-2,2'-dipyridyl; 5-(thiapentyl)-1,10-phenanthroline; tri-n-butylamine, and the like.

Additional organic nitrogen ligands suitable in the present invention include ethanolamine; diethanolamine; isopropanolamine; di-n-propanolamine; N,N-dimethylglycine; N,N-diethylglycine; N-methyliminodiacetic acid; N-methyldiethanolamine; 2-hydroxypyridine; methyl-substituted 2-hydroxypyridine; picolinic acid; methyl-substituted picolinic acid; nitrilotriacetic acid; N-(2-hydroxyethyl)iminodiacetic acid; ethylenediaminetetraacetic acid; 2,6-dicarboxypyridine; 8-hydroxyquinoline; 2-carboxyquinoline; cyclohexane-1,2-diamine-N,N,N',N'-tetraacetic acid; the tetramethyl ester of ethylenediaminetetraacetic acid, and the like.

Other suitable ligands include: methyl urea; 1,3-diphenyl urea; 1,1-dimethyl urea; 1,1,3,3-tetraethyl urea; N,N'-dimethylaniline; ortho-N,N'-dimethylaminophenol; 2-cyanoethyldimethylamine; 3-cyanopyridine; 2,3-dihydroxypyridine; lepidine; 2,4-lutidine; pyridazine; pyrazine; 2-pyridylacetonitrile; 2,2'-biquinoline; and tropine.

It should be understood that there are two definitions of the term "Lewis base nitrogen compound": (a) nitrogn compounds actually having basic properties as indicated by reactivity with acids, and (b) those which, regardless of basicity, can form coordination compounds as explained above. The latter, broader, definition is intended to apply in the present specification.

The catalyst comprising the cobalt carbonyl in complex combination with an organic nitrogen ligand may be formed *in situ* or *ex situ*, it only being necessary that the ligand and a cobalt carbonyl be contacted with each other. The cobalt carbonyl itself may be added as a cobalt carbonyl or may be formed *in situ* from a catalyst compound which will form cobalt carbonyl under reaction conditions. Cobalt acetate, cobalt napthenate and cobalt carbonate are examples of compounds which under reaction conditions will form a cobalt carbonyl. When a cobalt carbonyl is used as a source of the catalyst, dicobalt octacarbonyl or cobalt hydrocarbonyl is preferred although tetracobalt dodecacarbonyl may also be used. It is believed that cobalt hydrocarbonyl, $HCo(CO)_3$ or $HCo(CO)_4$, is the active form and that other cobalt carbonyls and the above mentioned cobalt salts are converted to cobalt hydrocarbonyl under reaction conditions. The inventor does not, however, wish to be held to any particular theory of the mechanism.

The quantity of catalyst employed is not narrowly critical and can vary over a wide range. In general, the process is desirably conducted in the presence of a catalytically effective quantity of the complex catalyst, which gives a suitable and reasonable reaction rate. Generally, an amount of catalyst should be used which will provide from about 0.5 to 100 millimoles, preferably about 2 to 50 millimoles, of cobalt carbonyl calculated as dicobalt octacarbonyl, $Co_2(CO)_8$, per mole of methanol although higher amounts up to solubility limits of the catalyst may be used. The amount of nitrogen ligand should be such as to provide an atomic ratio of Lewis base nitrogen atoms to cobalt atoms of about 1:1, although satisfactory results can be obtained where such atomic ratio is within the range of 0.3:1 to 3.0:1, especially 0.5:1 to 2.0:1, Lewis base nitrogen atoms per cobalt atom. The basic conditions for the reaction of the methanol with the synthesis gas are well known. Preferably, the methanol in a liquid phase containing the dissolved catalyst is intimately contacted with the synthesis gas by bubbling the gas through the liquid. The reaction temperature can vary over a wide range of elevated temperatures. In general, the process can be conducted at a temperature from about 150° to 250° C., best results obtaining within the range of about 175° to 215° C.

The process is suitably effected over a wide superatmospheric pressure range. The pressure must be at least sufficient to maintain a liquid phase of the methanol at the reaction temperature involved and generally should not be below about 20 atmospheres absolute. Pressures below about 20 atmospheres absolute may result in deterioration of the complex catalyst. Generally, a pressure within the range of about 20 to 700 atmospheres absolute should be used, although pressures within the range of about 130 to 400 atmospheres absolute are preferred.

The reaction is allowed to proceed for a period of time sufficient to form the desired methyl acetate, acetaldehyde and/or dimethyl acetal products. In general, the residence time can vary from a few minutes to several hours, but generally the reaction time should be about 1 to 10 hours, with times of about 3 to 7 hours preferred. The proper residence time will of course vary with such factors as temperature, pressure, catalyst concentration, and the particular catalyst being used.

The composition of any particular synthesis gas will vary according to the source thereof although the composition or source is not particularly critical to the present invention. The relative amounts of carbon monoxide and hydrogen which are present in the gas to be reacted with the methanol can be varied over a wide range. A typical synthesis gas will contain from about 30 to 60 mole percent of carbon monoxide and 40 to 70 mole percent of hydrogen, and such is a preferred mixture for the process. However, mixtures of hydrogen and carbon monoxide containing from about 10 to 90 mole percent carbon monoxide and 90 to 10 mole percent hydrogen will also be satisfactory for practice of the invention.

The process can be executed in a batch, semi-continuous, or continuous fashion. It can be conducted in a single reaction zone or a plurality of reaction zones, in series or in parallel, or it may be conducted intermittently or continuously in an elongated tubular zone or series of such zones. The catalyst may be initially introduced into the reaction zone batchwise, or it may be continuously or intermittently introduced into such zone during the course of the reaction.

Methyl acetate, acetaldehyde and dimethyl acetal can be recovered from the liquid product stream by several techniques well known in the art including fractional distillation, azeotropic distillation, etc. either directly from the liquid product or after extraction of the desired products into a suitable solvent. The recovered unreacted methanol (if the process is operated at less than 100% methanol conversion) as well as some light ends such as dimethyl ether can advantageously be recycled back to the reactor as part of the methanol feed. In addition, methyl acetate and dimethyl acetal, if desired, could be hydrolyzed to acetic acid and methanol or acetaldehyde and methanol with the recovered methanol being recycled as part of the methanol feed.

The cobalt catalyst can be recycled or recovered and converted to a convenient catalyst or catalyst precursor form before recycling by a number of techniques well known in the art. For example, after recovery of the desired products and unreacted methanol and removal of water from the liquid product stream, the remaining heavy ends, which contain the cobalt catalyst in a concentrated form, could be recycled directly to the reactor. Alternatively, the heavy ends plus cobalt catalyst could be passed through an ion-exchange resin to recover the cobalt, or base added to precipitate the cobalt as a cobalt hydroxide or a suitable solvent added to extract the cobalt from the heavy ends phase if the heavy ends are unsuitable for recycle. As stated before, the cobalt catalyst need not be recycled in the form of cobalt hydrocarbonyl or dicobalt octacarbonyl, but may be a precursor that would form the cobalt carbonyl catalyst under reaction conditions.

EXAMPLE I

To a 300 milliliter stainless steel reactor capable of withstanding internal pressures of at least 340 atmospheres were charged 64.1 grams of methanol, 6.8 grams of dicobalt octacarbonyl, and 1.9 grams of glutaronitrile. No source of halide moiety of any sort was present in this example nor in any of the examples which follow hereinbelow. The reactor was purged of air and pressured to about 220 atmospheres with synthesis gas composed of about 50 mole percent carbon monoxide and 50 mole percent hydrogen. The reactor was heated rapidly to about 180° C. while the reactants were continually agitated by rocking the reactor up and down. The pressure in the system reached a maximum of about 290 atmospheres. Upon reaching the reaction temperature, the course of the reaction was followed by observing the decrease in pressure in the system. When the pressure had dropped to about 165 atmospheres (approximately four hours after reaching reaction temperature), the reaction was stopped. After cooling to ambient temperature, the final pressure in the system was about 103 atmospheres and 86.3 grams of liquid product was recovered. The analysis of the liquid product showed it to contain, by weight, about 13.0 percent methyl acetate, 7.0 percent combined acetaldehyde and dimethyl acetal, 3.8 percent ethanol, 54.4 percent methanol and 16.7 percent water, the remainder being various minor amounts of oxygenated hydrocarbons. The molar carbon efficiency for methyl acetate was calculated to be 42 mole percent and the molar carbon efficiency for the combined acetaldehyde and dimethyl acetal was calculated to be about 18 mole percent. The molar carbon efficiencies were calculated based on the total moles of reacted carbon monoxide and on a carbon accounted for basis.

When the same experiment is repeated, except that no glutaronitrile ligand is added, the amount of methyl acetate in the liquid product will be only about 3.1 percent by weight and the combined acetaldehyde and dimethyl acetal will be only about 5.2 percent by weight. The molar carbon efficiency for the methyl acetate produced would be only about 13 mole percent, while the carbon efficiency of the acetaldehyde and dimethyl acetal combined would be about 18 mole percent.

EXAMPLE II

The procedure of Example I was repeated except that the charge to the reactor consisted of 64.1 grams of methanol, 3.4 grams of dicobalt octacarbonyl and 3.1 grams of ortho-phenylenediacetonitrile. The molar carbon efficiency to methyl acetate was about 30 mole percent and the molar carbon efficiency of the combined acetaldehyde and dimethyl acetal produced was about 34 mole percent.

EXAMPLE III

The procedure of Example I was repeated except that the charge to the reactor consisted of 64.1 grams of methanol, 6.8 grams of dicobalt octacarbonyl and 7.6 grams of 2-hydroxypyridine. The molar carbon efficiency to methyl acetate was about 44 mole percent and the molar carbon efficiency of the combined acetaldehyde and dimethyl acetal produced was about 10 mole percent.

EXAMPLE IV

The procedure of Example I was repeated except that the charge to the reactor consisted of 64.1 grams of methanol, 6.8 grams of dicobalt octacarbonyl and 2.3 grams of tetramethylethylenediamine. The molar carbon efficiency to methyl acetate was about 38 mole percent and the molar carbon efficiency of the combined acetaldehyde and dimethyl acetal produced was about 22 mole percent.

EXAMPLE V

The procedure of Example I was repeated except that the charge to the reactor consisted of 64.1 grams of methanol, 3.4 grams of dicobalt octacarbonyl and 4.7 grams of 2-cyanophenol. The molar carbon efficiency to methyl acetate was about 30 mole percent and the molar carbon efficiency of the combined acetaldehyde and dimethyl acetal produced was about 15 mole percent.

EXAMPLE VI

The procedure of Example I was repeated except that the charge to the reactor consisted of 64.1 grams of methanol, 3.4 grams of dicobalt octacarbonyl and 1.2 grams of urea. The molar carbon efficiency to methyl acetate was about 23 mole percent and the molar carbon efficiency of the combined acetaldehyde and dimethyl acetal produced was about 35 mole percent.

The embodiments of the invention in which an exclusive privilege is claimed are defined as follows:

1. In a process for reacting methanol in the liquid phase at elevated temperature and superatmospheric pressure with a gas comprising carbon monoxide and hydrogen to form a product comprising methyl acetate, acetaldehyde, and dimethylacetal, the improvement which comprises utilizing a catalytic amount of a halide-free catalyst consisting essentially of a cobalt carbonyl in complex combination with an organic nitrogen ligand of from one to 25 carbon atoms having no ethylenic or acetylenic unsaturation and no elements other than carbon, nitrogen, oxygen, and hydrogen, said ligand containing in its molecule from 1 to 5 Lewis base nitrogen atoms which are present as urea, tertiary amino or nitrilo nitrogen atoms, said ligand being, when said nitrogen atoms are urea nitrogens, a urea of the formula

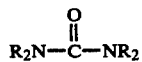

wherein R is hydrogen or a $C_1$ to $C_9$ hydrocarbon group and wherein each R group may be alike or different.

2. In a process for reacting methanol in the liquid phase at elevated temperature and superatmospheric pressure with a gas comprising carbon monoxide and hydrogen to form a product comprising methyl acetate, acetaldehyde, and dimethylacetal, the improvement which comprises utilizing a catalytic amount of a halide-free catalyst consisting essentially of a cobalt carbonyl in complex combination with an organic nitrogen ligand of from one to 25 carbon atoms having no ethylenic or acetylenic unsaturation and no elements other than carbon, nitrogen, oxygen, and hydrogen and which is a member of the group consisting of glutaronitrile, ortho-phenylenediacetonitrile, 2-hydroxypyridine, tetramethylethylenediamine, 2-cyanophenol, and urea.

3. In a process for reacting methanol in the liquid phase at elevated temperature and superatmospheric pressure with a gas comprising carbon monoxide and hydrogen to form a product comprising methyl acetate, acetaldehyde, and dimethylacetal, the improvement which comprises utilizing a catalytic amount of a halide-free catalyst consisting essentially of a cobalt carbonyl in complex combination with an organic nitrogen ligand of from one to 25 carbon atoms having no ethylenic or acetylenic unsaturation and no elements other than carbon, nitrogen, oxygen, and hydrogen and which is a member of the group consisting of dinitriles having from 3 to 18 carbon atoms and ureas of the formula $R_2NCONR_2$ wherein R is hydrogen or a $C_1$ to $C_9$ hydrocarbon group and wherein the R groups may be alike or different.

4. The improvement of claim 3 wherein an amount of said catalyst is used which will provide from about 2 to 50 millimoles of cobalt carbonyl, calculated as dicobalt octacarbonyl, per mole of methanol; the amount of said nitrogen ligand is such as to provide an atomic ration of nitrogen atoms to cobalt atoms of from about 0.5:1 to 2.0:1; the process is conducted at about 175° to 215° C. and about 130 to 400 atomspheres absolute; and said gas comprises about 30 to 60 mole percent carbon monoxide and 40 to 70 mole percent hydrogen.

5. In a process for reacting methanol in the liquid phase at elevated temperature and superatmospheric pressure with a gas comprising carbon monoxide and hydrogen to form a product comprising methyl acetate, acetaldehyde, and dimethylacetal, the improvement which comprises utilizing a catalytic amount of a halide-free catalyst consisting essentially of a cobalt carbonyl in complex combination with a urea of the formula $R_2NCONR_2$ wherein R is hydrogen or a $C_1$ to $C_9$ hydrocarbon group and wherein the R groups may be alike or different, the amount of said catalyst used being such as to provide from about 2 to 50 millimoles of cobalt carbonyl, calculated as dicobalt octacarbonyl, per mole of methanol and the amount of said urea being such as to provide an atomic ratio of nitrogen atoms to cobalt atoms of from about 0.5:1 to 2.0:1, said process being conducted at about 175° to 215° C. and about 130 to 400 atmospheres absolute and said gas comprising about 30 to 60 mole percent carbon monoxide and 40 to 70 mole percent hydrogen.

6. The improvement of claim 5 wherein said urea is $H_2NCONH_2$.